(12) United States Patent
Ono (10) Patent No.: US 6,549,809 B2
(45) Date of Patent: Apr. 15, 2003

(54) FAR INFRARED RADIATION HEALTH APPLIANCE AND METHOD OF USE

(75) Inventor: Hisata Ono, Tokyo (JP)

(73) Assignee: Patent Kaihatsu Co., Ltd., Tokyo (JP)

( * ) Notice: Subject to any disclaimer, the term of this patent is extended or adjusted under 35 U.S.C. 154(b) by 17 days.

(21) Appl. No.: 09/829,550

(22) Filed: Apr. 10, 2001

(65) Prior Publication Data

US 2002/0183814 A1 Dec. 5, 2002

(51) Int. Cl.⁷ .................................................. A61F 2/00
(52) U.S. Cl. ....................... 607/100; 607/88; 607/91; 607/96; 606/9; 606/27; 4/536
(58) Field of Search .................... 607/81, 83, 88, 607/90, 91, 96, 100; 606/9, 10, 27; 4/524, 535, 536

(56) References Cited

U.S. PATENT DOCUMENTS 5,255,399 A * 10/1993 Park ............................ 4/525
6,004,344 A * 12/1999 Fujii ............................ 607/91
6,272,697 B1 * 8/2001 Park ............................ 4/524
6,327,506 B1 * 12/2001 Yogo et al. .................. 607/100
6,327,720 B1 * 12/2001 Kim ............................ 4/524
6,363,285 B1 * 3/2002 Wey ............................ 607/100
6,418,573 B1 * 7/2002 Masuda ........................ 4/538

FOREIGN PATENT DOCUMENTS

| EP | 0 143 645 | 11/1984 |
| EP | 0 693 683 | 1/1996 |
| EP | 0 837 356 | 4/1998 |

* cited by examiner

*Primary Examiner*—Pamela Wilson
(74) *Attorney, Agent, or Firm*—Norris McLaughlin & Marcus

(57) ABSTRACT

A far infrared radiation health appliance which can effectively stimulate sebaceous glands together with perspiratory glands for dioxins egestion. The appliance includes a plurality of semicylindrical members to be axially coupled to each other in a bush-like manner, and carbon-black-containing planar heating elements arranged over the general entire inner surfaces thereof. The planar heating elements are energized and heated to a temperature of 55–70° C.

17 Claims, 7 Drawing Sheets

FAR INFRARED RADIATION HEALTH APPLIANCE AND METHOD OF USE

BACKGROUND OF THE INVENTION

1. Field of the Invention

The present invention relates to a far infrared radiation health appliance, far infrared radiation health method, and a method for egesting dioxins and active oxygen sources.

2. Description of the Related Art

Conventionally, there has been known a so-called far infrared radiation sauna for irradiating a whole body with far infrared radiation to promote blood circulation and perspiration. This far infrared circulation sauna is taken with the whole body put in a sealed housing, or only the head out. The whole body is heated up by far infrared radiation heating means arranged in the box.

In general, conventional saunas have had the following defects.

(1) A users is set on a chair arranged in the housing when heated to high temperatures for forced perspiration. This unfavorably stimulates the blood circulation and muscles of the whole body while the body is strained. Besides, no sebaceous gland will be stimulated together with perspiratory glands in the skin.

(2) Despite the use for the sake of health, the saunas provide such a temperature condition that one's head is at a high temperature and the feet are at a low temperature, or a condition of keeping one's head warm and feet cool, which contradicts a first principle of health "keeping one's head cool and feet warm. Thus, the saunas cannot be taken in conformity to the principle of health.

(3) The bathing in an enclosed room increases the risk of inspiring the oxygen-deficient air aspired by others or of getting infected with resistant tubercle bacilli through aerial infection.

(4) Lower-half bathing is impossible, whereas the lower-half bathing is sometimes effective at reducing invasiveness.

(5) The saunas are incapable of light bathing which improves the blood circulation and promotes metabolism without perspiration.

(6) A lie-down, 24-hour continuous use is impossible.

(7) Cannot be used by those who are sick or bedridden.

SUMMARY OF THE INVENTION

An object of the present invention is to provide a health appliance and a health method free of such defects of the conventional saunas, and more particularly to provide a far infrared radiation health appliance and a far infrared radiation health method in which sebaceous glands as well as perspiratory glands can be stimulated effectively.

Moreover, in recent years, there has been a growing interest in dioxins as environmental pollutants. Dioxins, a generic name of polychlorinated dibenzo-p-dioxins (PCDD) and polychlorinated dibenzofurans (PCDF), are generated in the process of chemical synthesis or in the process of combustion. The dioxins are nonpolar fat-soluble organic substances, having high acute toxicity 1000 times that of potassium cyanide, as well as a wide range of toxicity including carcinogenecity, generation toxicity, immunological toxicity, and endocrinopathy. The dioxins, when taken into a human body, are mainly stored into fat tissue. Accordingly, while immediate egestion out of a body is required of dioxins that are ingested and stored in a body, there has been no appropriate method therefor due to the poor metabolizability of the dioxins.

It is thus another object of the present invention to provide a method for egesting dioxins and/or active oxygen sources ingested and stored in a body to outside the body effectively.

A far infrared radiation health appliance according to the present invention includes a plurality of semicylindrical members to be axially connected to each other in a bush-like manner, and carbon-black-containing planar heating elements for serving as resistors arranged over the general entire inner surfaces of the cylindrical members. The planer heating elements are energized and heated to a temperature of 55–70° C., and preferably a temperature of 60–65° C.

A far infrared radiation health method according to the present invention includes the step of making a far infrared irradiation to promote perspiration from perspiratory glands and egestion of sebum from sebaceous glands.

Another far infrared radiation health method according to the present invention includes the step of irradiating a body surface with far infrared rays from a carbon-black-containing planar heating element energized and heated to a temperature of 55–70° C., thereby promoting perspiration from perspiratory glands and egestion of sebum from sebaceous glands.

Another far infrared radiation health method according to the present invention includes the step of adjusting a power supply to a planer heating element for radiating far infrared rays, so that the interior of an enclosed dome is adjusted to a temperature not causing perspiration or a temperature right below the point of perspiration for use. The user puts the whole body, or a part, into the semiclosed dome for far infrared irradiation.

A method for egesting dioxins according to the present invention includes the step of egesting dioxins together with perspiration and sebum from perspiratory glands by using the far infrared radiation health method described above.

Human skin is an organ which has such apparatuses as perspiratory glands and sebaceous glands, and occupies 16% of the whole body. As the temperature rises, a human exudes perspiration. This perspiration is egested from perspiratory glands. The perspiration egested from perspiratory glands is of almost the same quality as urine, containing such ingredients as water, sodium chloride, uric acid, ammonia, amino acid, potassium, creatine, and urea. In addition to a rise in temperature, the perspiration from perspiratory glands is also promoted by bathing, sauna bathing, exercise, the taking of antipyretics, and so on.

Meanwhile, sebaceous glands store and egest the same fat as body fat, covering the skin with fat for protection. The perspiration (sebum) from sebaceous glands contains cholesterol, fatty ester, lactic acid, excessive subcutaneous fat, and so on. It is like exudation of human fat/body fat. Moreover, it is said that body fat stores mercury, cadmium, lead and other heavy metals taken into the body through ingested food, drinks, respiration, or percutaneous means, as well as chemicals much talked about nowadays as environmental hormones (extrinsic endocrine disrupting chemicals), carcinogens, and the like. Promoting the egestion of sebum perspiration from sebaceous glands makes it possible to egest such toxic substances dissolved in the body fat to outside the body. Dioxins, known as having a wide range of toxicity such as high acute toxicity, carcinogenecity, generation toxicity, immunological toxicity, and endocrinopathy, are also stored in fat tissue.

Therefore, the promoted egestion of sebum perspiration from sebaceous glands also allows the effective egestion of these dioxins dissolved in body fat to outside the body.

The sebum egestion from sebaceous gland cannot be promoted by bathing, saunas, or exercise. Nevertheless, when cells of a living body are irradiated with far infrared rays having a wavelength of 5–20 $\mu$m, which is most favorable for resonance, and resonance absorption phenomena deliver the far infrared rays deep into the body to stimulate sebaceous glands, it becomes possible to promote the sebum egestion. The carbon black planer heating elements energized and heated to a temperature of 55–70° C., or preferably a temperature of 60–65° C., by resistance heating can effectively generate the far infrared rays resonance-absorbable to the cells of a living body, thereby effectively stimulate sebaceous glands.

As described above, according to the far infrared radiation health appliance of the present invention, the cutaneous function can be activated to improve the cutaneous respiration and blood circulation for more active metabolism, thereby promoting two types of perspiration, namely, high volume of perspiration from perspiratory glands and sebum perspiration from sebaceous glands. In particular, toxic substances (including dioxins) stored in the body can be egested from sebaceous glands effectively to contribute to health enhancement.

Moreover, when the interior of the enclosed dome is adjusted to a temperature causing no perspiration or a temperature right below the point of perspiration for use, the body temperature is at best increased to 38° C. or so, and maintained without perspiration. According to the latest theories from American Association of Immunologists, a 1° C. rise of body temperature means a 6-times leukocyte immunoactivity. Given that the normal temperature is 36.5° C., the body temperature increased and maintained to 38° C. results in an immunoactivity of (38−36.5=1.5° C.), or 6×6/2=18 times. This is of great help to improve self healing power against bad diseases.

The nature, principle, and utility of the invention will become more apparent from the following detailed description when read in conjunction with the accompanying drawings.

DETAILED DESCRIPTION OF THE PREFERRED EMBODIMENT

Figure 1:
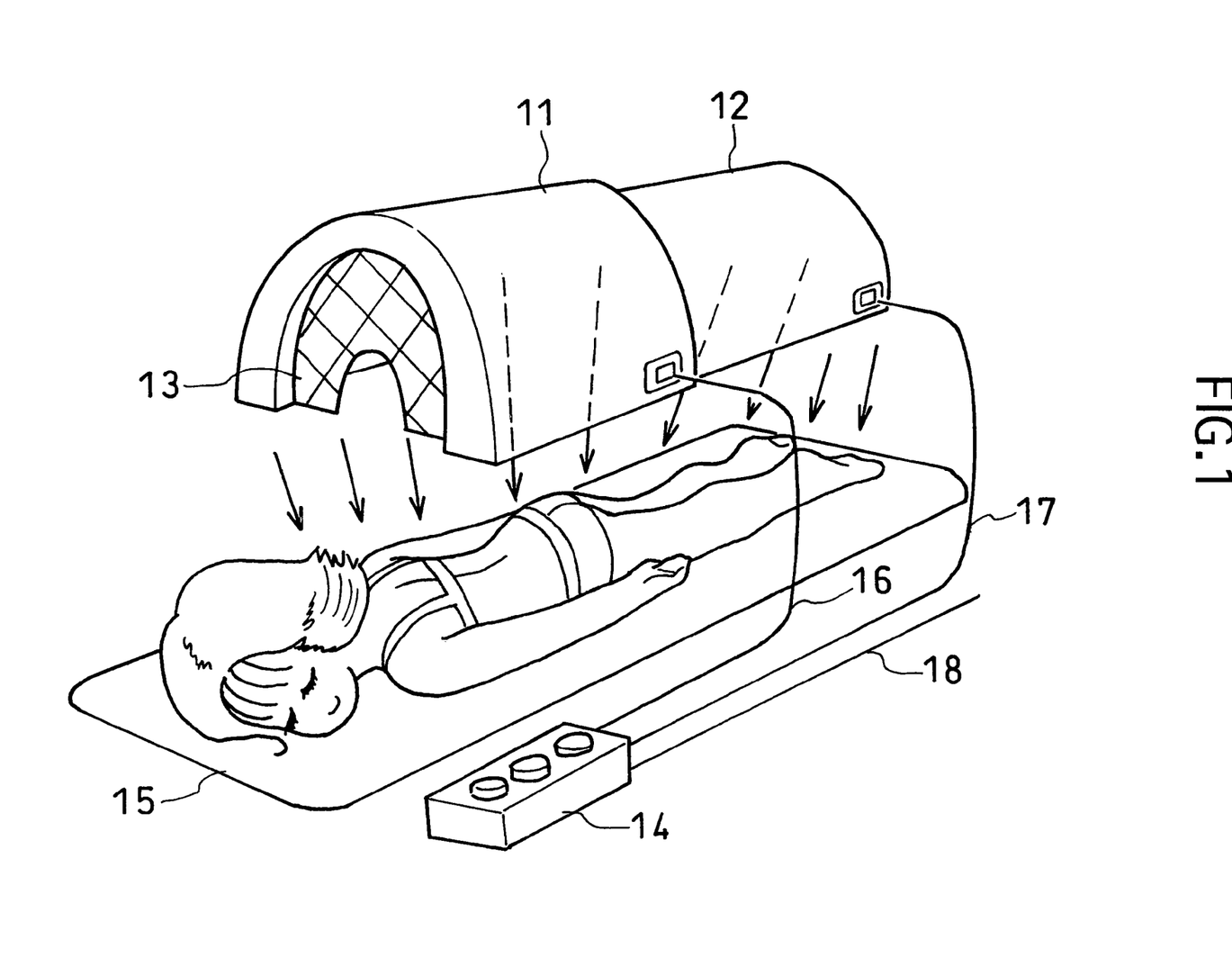
FIG. 1 is a schematic diagram explaining the general diagram of a far infrared radiation health appliance according to the present invention.
Figure 2:
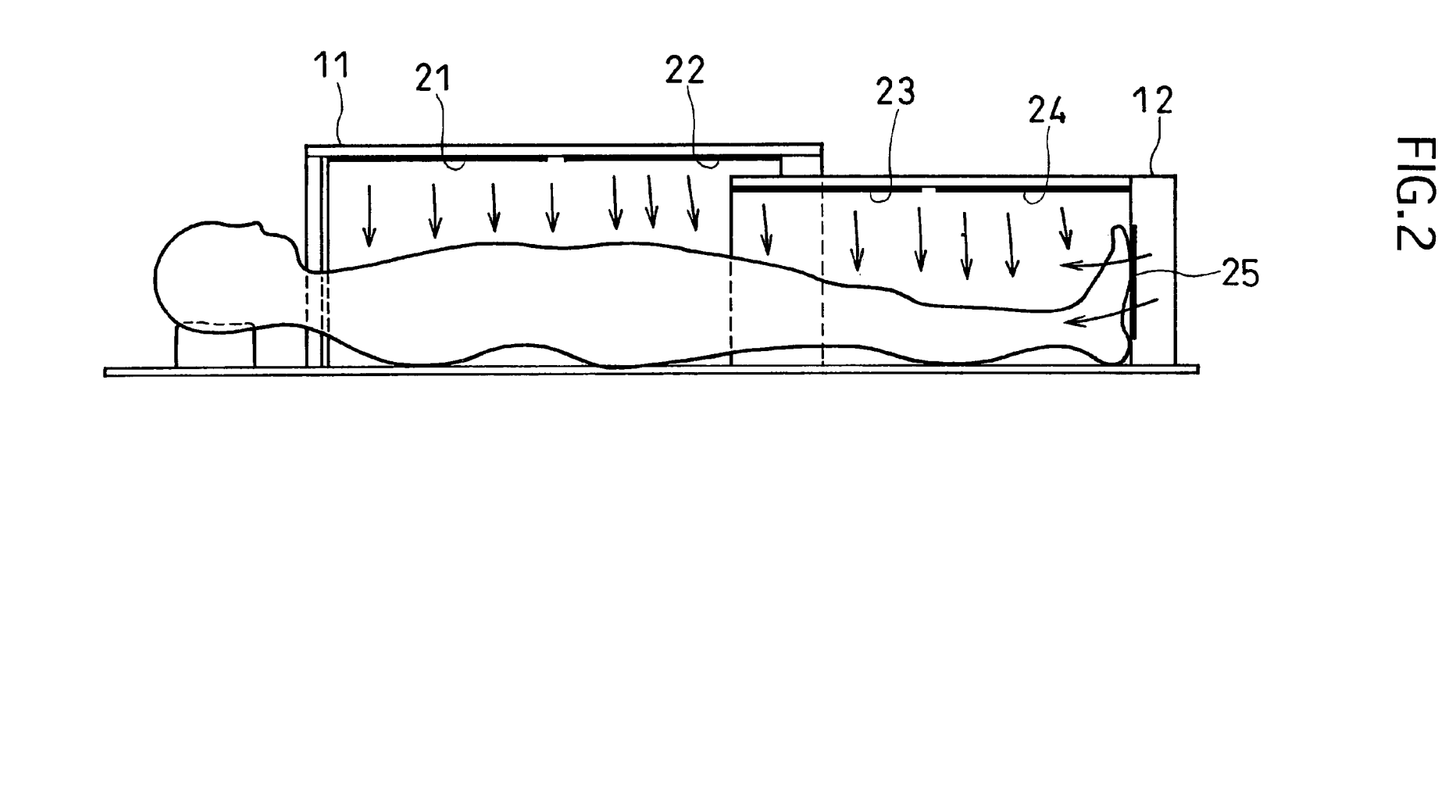
FIG. 2 is a cross-sectional schematic diagram of service conditions.
Figure 3A:
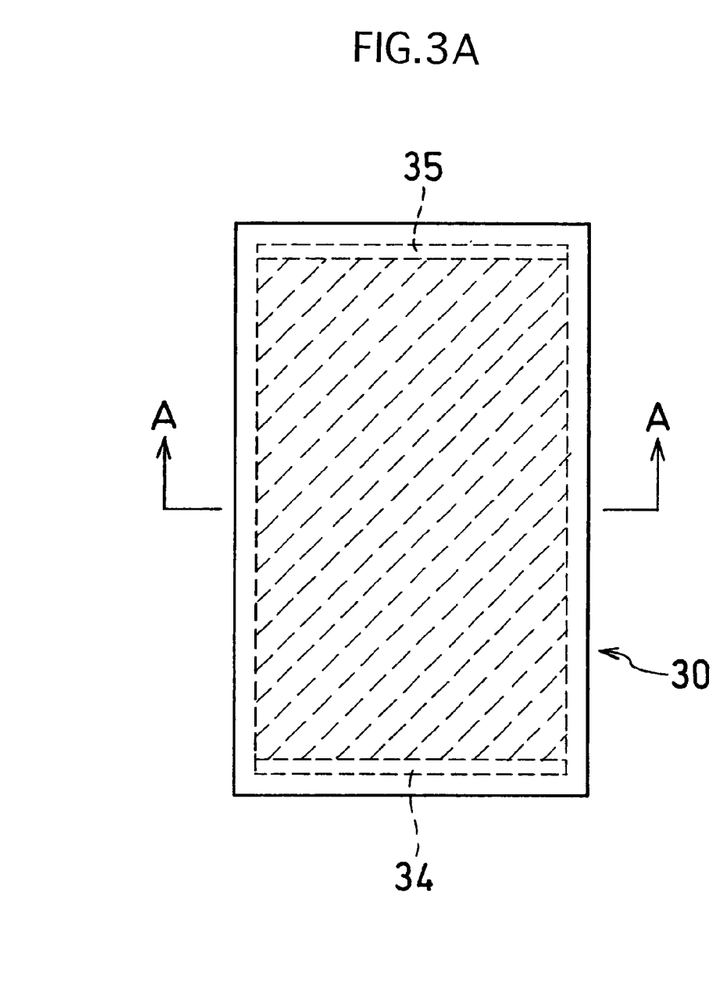
FIGS. 3A and 3B are explanatory diagrams of a panel heater (planar heating element)
Figure 3B:
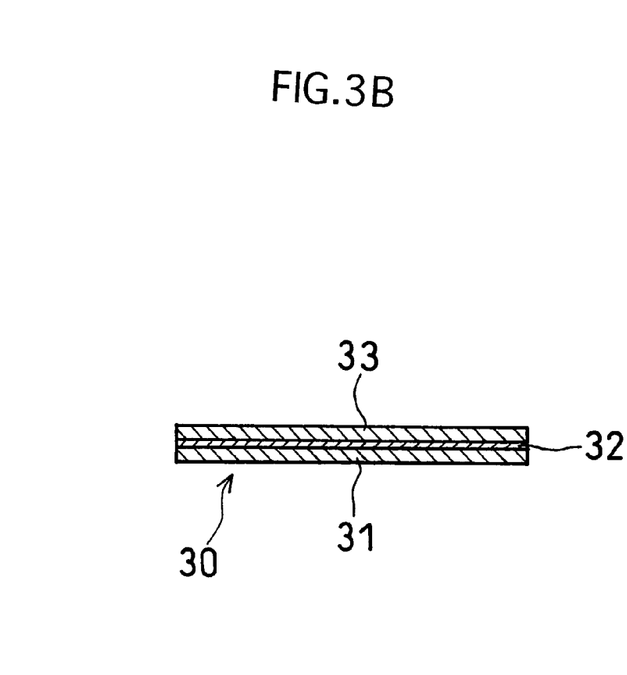
Figure 4A:
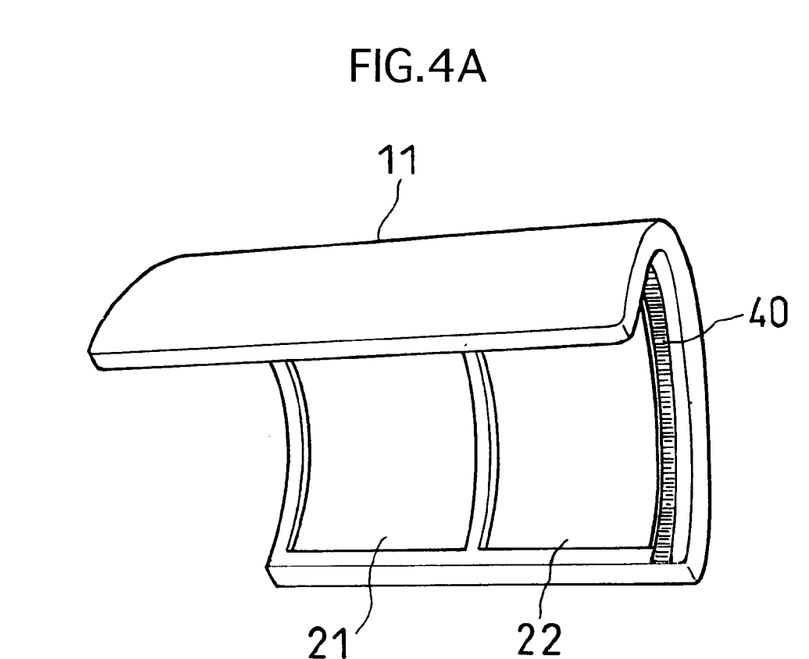
FIGS. 4A and 4B are detailed view of an upper dome.
Figure 4B:
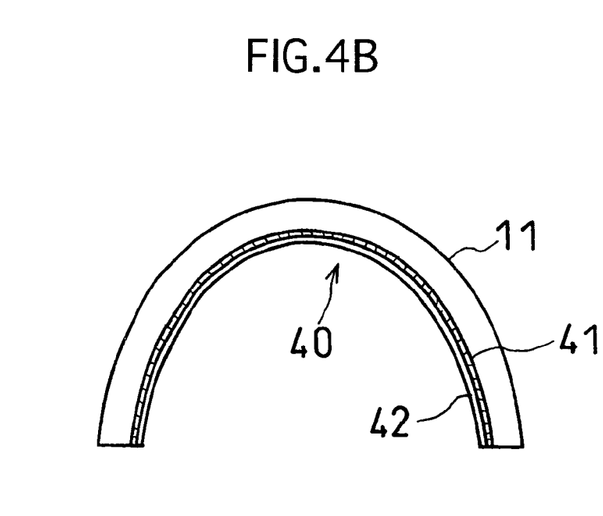
Figure 4C:
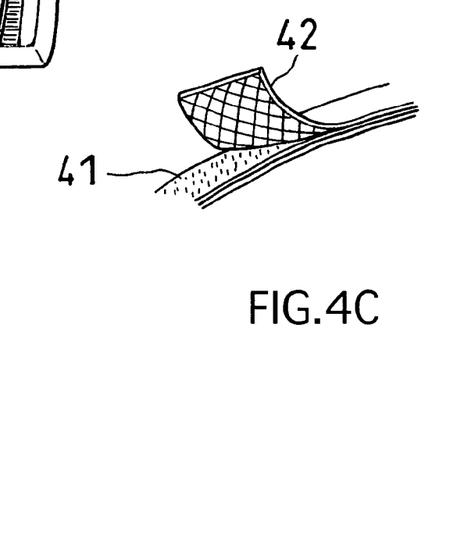
Figure 5:
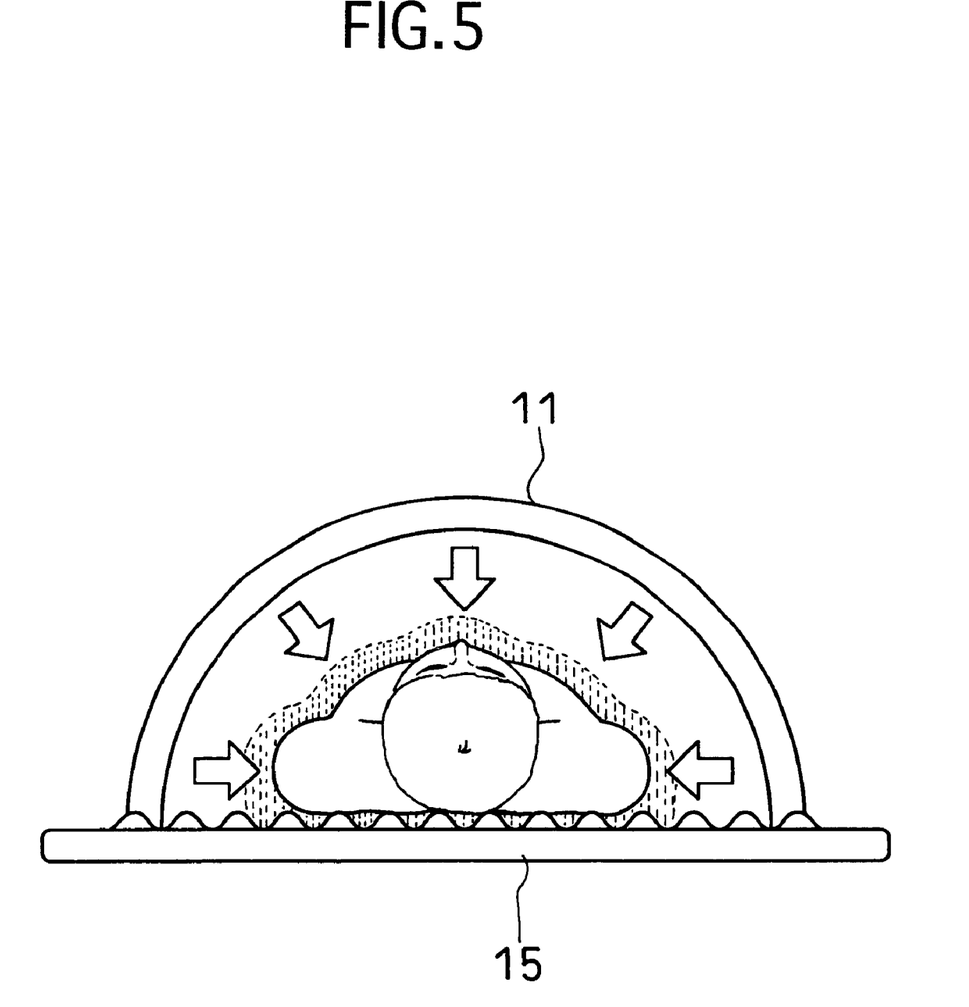
FIG. 5 is a longitudinal sectional schematic diagram of service conditions.

Hereinafter, an embodiment of the present invention will be described with reference to the drawings. FIG. 1 is a schematic diagram explaining the general configuration of a far infrared radiation health appliance according to the present invention. FIG. 2 is a cross-sectional schematic diagram of the appliance under service conditions. FIGS. 3A and 3B are explanatory diagrams of a panel heater (planar heating element). FIGS. 4A–4C are detailed views of an upper dome. FIG. 5 is a longitudinal sectional schematic diagram of service conditions.

As simplified in FIG. 1, this far infrared radiation health appliance has an upper dome 11 and lower dome 12 of semicylindrical shape. A user lies in the internal space formed by the upper and lower domes 11, 12 and a sheet 15 reflecting far infrared rays on the floor. The lower dome 12 has the shape of a semicylinder with a diameter smaller than that of the upper dome 11. The upper dome 11 and the lower dome 12 are coupled to each other so that they can be moved in a bush-like manner along the axial direction of the domes as semiclosed. Therefore, the length of the entire dome consisting of the upper dome 11 and the lower dome 12 can be adjusted to the height of the user. Besides, the entire dome can be conveniently reduce to about a half in volume when put away. An end of the lower dome 12 is closed by a half-round plate. Electric cords 16 and 17 are extended from the upper and lower domes 11 and 12, respectively. These cords are connected to a controller 14. The controller 14 is, in turn, connected through an electric cord 18 to a power supply such as a wall outlet.

The upper dome 11 has at one end a neck cover 13, with which the neck of the user is covered softly to keep the dome interior semiclosed. The neck cover 13 may be formed of cloth. Far infrared ray reflective coating may be applied to the surface of the neck cover 13 which faces the dome interior. The far infrared ray reflective coating is achieved, for example, by sewing on an aluminum deposition sheet or the like that reflects far infrared rays. The user lies on a towel or the like put on the floor sheet 15. The floor sheet 15 preferably consists of an aluminum-evaporated urethane sheet or other material that reflects far infrared radiation. The user may take any posture, such as face up, on the side, and face down. A full bath with head, full bath without head, half bath, lower half bath, foot bath, or the like may be taken freely. In the cases of stiffness on the back or the lower back, face-down use would be effective. Such usage is impossible in conventional saunas.

Panel heaters for radiating far infrared rays are arranged almost all over the inner surfaces of the upper and lower domes 11 and 12. In the shown example, the upper dome 11 has two panel heaters 21 and 22 along its curved inner surface (see FIGS. 2 and 4A). The lower dome 12 also has two panel heaters 23 and 24 along its curved inner surface, as well as a panel heater 25 on the half-round end. The two panel heater 21 and 22 arranged on the upper dome 11 typically irradiate the chest (back) and abdomen (lower back and buttocks) of the user lying inside the dome with far infrared rays. The three panel heaters 23, 24, and 25 irradiate the femoral regions, anticnemions/calves, and soles of the user with far infrared rays.

FIGS. 3A and 3B are explanatory diagrams of a panel heater used in the present invention. FIG. 3A is a plan view, and FIG. 3B a sectional view taken along the line A—A. As shown in the sectional view of FIG. 3B, this panel heater 30 has a three-layer structure including two sheets 31 and 33 sandwiching a carbon black layer 32. The panel heater has electrodes 34 and 35 on both ends, in contact with the carbon black layer 32. When the carbon black layer 32 is energized through the electrodes 34 and 35, the entire carbon black layer 32 heats up by resistance heating, thereby radiating far infrared rays. In the present invention, the power to the panel heaters is adjusted so that the panel heaters reach 60° C. in temperature. The adjustment can be made separately to the upper dome 11 and to the lower dome 12. The heater temperature can be fine adjusted by operating the controller 14. Moreover, the controller 14 has a timer function which can be used to set the energizing time of the panel heaters.

As shown in FIGS. 4A and 4B, the upper dome 11 has a sealing mechanism 40 arranged on the underside of its end overlapping the lower dome 12. The sealing mechanism 40 seals the gap formed with the topside of the lower dome 12. This sealing mechanism 40 consists of a hook-side Velcro fastener 41 tacked to the inner end surface of the upper dome 11, and a felt-like tape 42 having a loop-side Velcro fastener stuck to its backside. By means of the engagement between the Velcro fasteners, the felt-like tape 42 having the loop-side Velcro fastener stuck to its backside is fixed to the underside of the end of the upper dome 11 with the felt-surface outside. This sealing mechanism 40 seals the gap between the bush-coupled upper and lower domes 11 and 12, and allows the dome space to be freely and smoothly adjusted in length as kept airtight. In the cases of felt deterioration after long-time use, the felt-like tape 42 having the loop-side Velcro faster stuck to its backside is all that can be replaced with a new one to recover the sealing capability.

The far infrared radiation health appliance of the present invention employs the configuration in which a user lies in the space formed by the semicylindrical upper and lower domes 11 and 12, and is irradiated with the far infrared rays from the panel heaters 21–25 arranged on the inner surfaces of the upper and lower domes 11 and 12. Therefore, as shown in the general sectional view of FIG. 5, the far infrared rays are applied onto the entire surface of the body, as the focus of a concave mirror falls on the center line of the body. When the user is lying on the far infrared ray reflective sheet 15, the far infrared rays not absorbed into the user's body can be reflected by the far infrared ray reflective sheet 15 for user re-irradiation, with a further improvement in the irradiation efficiency of the far infrared rays. This also means a certain degree of far infrared ray irradiation on portions of the body not facing the panel heaters directly.

The peak wavelength of the electromagnetic waves radiated from a heater can be calculated by the Wien's displacement law. Home sauna appliances now on the market often use ceramic heaters of 300–500° C. in surface temperature as their heat sources. For example, a rod heater having a surface temperature of 400° C. (673 K in absolute temperature) radiates infrared rays with a peak wavelength of 4.3 $\mu$m (2897/673=4.3). Effective radiation of 8-to-10-$\mu$m far infrared rays easier for a living body to resonance absorb requires the use of heaters having lower surface temperatures. For example, the carbon-black-containing planer heaters of the present invention, heated to 60° C. (333 K in absolute temperature), radiate far infrared rays with a peak wavelength of 8.7 $\mu$m (2897/333=8.7). Moreover, heaters of greater radiation areas are required for the sake of suppressing the surface temperature for calorie-efficient radiation. Accordingly, the panel heaters employed in the present invention, using carbon black as the resistors, are extremely reasonable and best suited for the purpose of irradiating a living body with far infrared rays to stimulate cutaneous cells.

The far infrared radiation health appliance according to the present invention is capable of effectively irradiating cells of a living body with far infrared rays having a most-absorbable wavelength of 5–20 $\mu$m. Therefore, it can stimulate skin's perspiratory glands to promote perspiration, and stimulate sebaceous glands to promote sebum egestion as well. This allows the artificial egestion of sebum which cannot be promoted by bathing, saunas, or exercise. Thus, it becomes possible to egest chemicals toxic to a human body, dissolved and stored in subcutaneous fat and body fat, to exterior along with sebum.

The following Table 1 shows the analyses of the gas chromatography mass spectrometry on the concentrations of dioxins contained in the egesta through the skin of the user while using the far infrared radiation health appliance of the present invention. Aside from the concentrations, the table shows toxicity equivalents. The amount of each sample was 50 ml. The toxicity equivalents (TEQ) were 2, 3, 7, 8-$T_4$CDD toxicity equivalents (pg-TEQ/ml). The toxicity equivalency factors were of I-TEF (International-Toxicity Equivalency Factor (WHO/IPCS, 1988)). As for the minimum limits of determination, 4–5 chlorinated compounds: 0.01 pg/ml, 6–7 chlorinated compounds: 0.02 pg/ml, and 8 chlorinated compounds: 0.05 pg/ml. These analyses show that the far infrared radiation health appliance of the present invention is effective at egesting dioxins in the body.

TABLE 1

| UNIT | CONCENTRATION MEASUREMENT 50 ml (pg/ml) | TOXICITY EQUIVALENCY FACTOR (1-TEF) | TOXICITY EQUIVALENT (TEQ) (pg-TEQ/ml) |
|---|---|---|---|
| 2, 3, 7, 8-$T_4$CDD | <0.01 | 1 | 0 |
| 1, 2, 3, 7, 8-$P_5$CDD | <0.01 | 0.5 | 0 |
| 1, 2, 3, 4, 7, 8-$H_6$CDD | <0.02 | 0.1 | 0 |
| 1, 2, 3, 6, 7, 8-$H_6$CDD | <0.02 | 0.1 | 0 |
| 1, 2, 3, 7, 8, 9-$H_6$CDD | <0.02 | 0.1 | 0 |
| 1, 2, 3, 4, 6, 7, 8-$H_7$CDD | 0.039 | 0.01 | 0.00039 |
| $O_8$CDD | 0.17 | 0.001 | 0.00017 |
| $PCDF_S$ TEQ | — | — | 0.00056 |
| 2, 3, 7, 8-$T_4$CDF | <0.01 | 0.1 | 0 |
| 1, 2, 3, 7, 8-$P_5$CDF | <0.01 | 0.05 | 0 |
| 2, 3, 4, 7, 8-$P_5$CDF | <0.01 | 0.5 | 0 |
| 1, 2, 3, 4, 7, 8-$H_6$CDF | <0.02 | 0.1 | 0 |
| 1, 2, 3, 6, 7, 8-$H_6$CDF | <0.02 | 0.1 | 0 |
| 1, 2, 3, 7, 8, 9-$H_6$CDF | <0.02 | 0.1 | 0 |
| 2, 3, 4, 6, 7, 8-$H_6$CDF | <0.02 | 0.1 | 0 |
| 1, 2, 3, 4, 6, 7, 8-$H_7$CDF | <0.02 | 0.01 | 0 |
| 1, 2, 3, 4, 7, 8, 9-$H_7$CDF | <0.02 | 0.01 | 0 |
| $O_8$CDF | <0.05 | 0.001 | 0 |
| $PCDF_S$ TEQ | — | — | 0 |
| Total TEQ | — | — | 0.00056 |
| $T_4CDD_S$ | 0.032 | | |
| $P_5CDD_S$ | 0.027 | | |
| $H_6CDD_S$ | 0.030 | | |
| $H_7CDD_S$ | 0.071 | | |
| $O_8$CDD | 0.17 | | |
| Total $PCDD_S$ | 0.33 | | |
| $T_4CDF_S$ | 0.045 | | |
| $P_5CDF_S$ | 0.032 | | |
| $H_6CDF_S$ | 0.032 | | |
| $H_7CDF_S$ | 0.035 | | |
| $O_8$CDF | <0.05 | | |
| Total $PCDF_S$ | 0.14 | | |
| $PCDD_S \cdot PCDF_S$ Total | 0.47 | | |

The far infrared radiation health appliance according to the present invention is also effective at egesting active oxygen sources in the body. A sauna-exuded perspiration A, a bath-exuded perspiration B, and perspirations C and D exuded in the far infrared radiation health appliance of the present invention were collected as samples, and were measured for induced active oxygen. The perspirations A–D were sampled by 200 μl, and mixed with 20 μl of 5,5'-dimethyl-1-Pyrrolia-N-oxide (DMPO) as the spin trapping agent for active oxygen species. Both before and after five minutes of ultraviolet irradiation, the samples were analyzed in an ESR spectrometer for spin adducts. The reason why the experiments were conducted on both the ultraviolet-irradiated and not is to draw a distinction between active oxygen already in the perspirations and active oxygen induced by ultraviolet irradiation.

Figure 6:
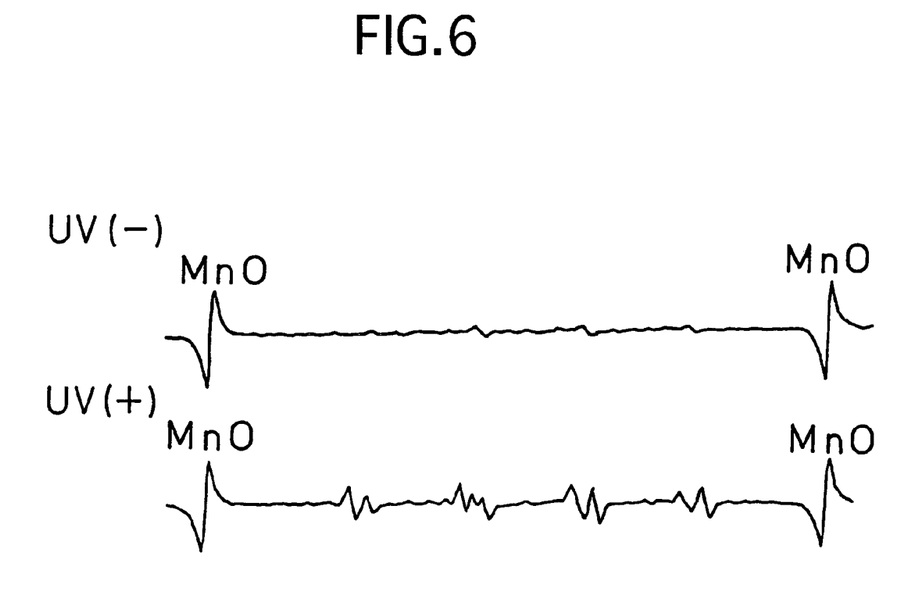
FIG. 6 is a chart showing the waveforms on perspiration A exuded in a dry sauna.
Figure 7:
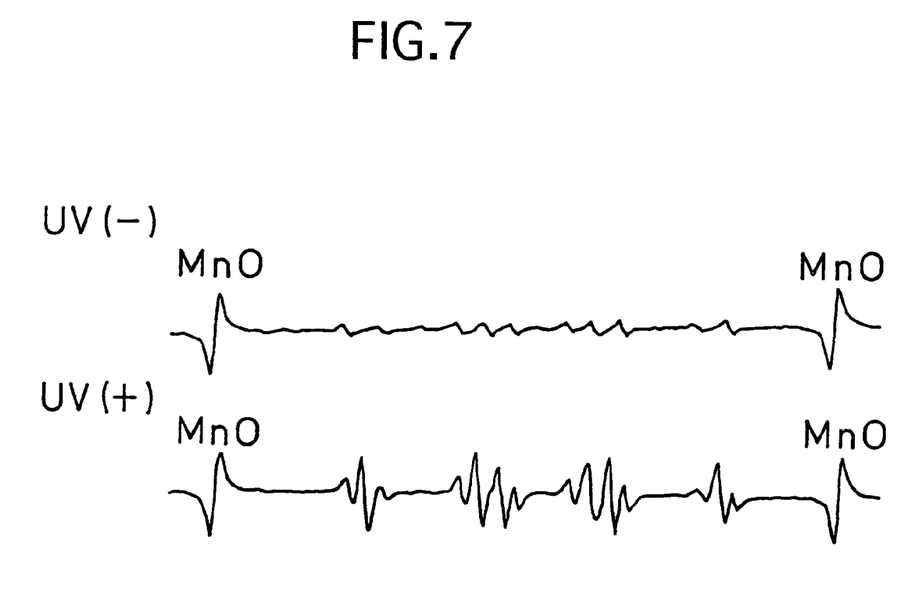
FIG. 7 is a chart showing the waveforms on perspiration B exuded in a bath.
Figure 8:
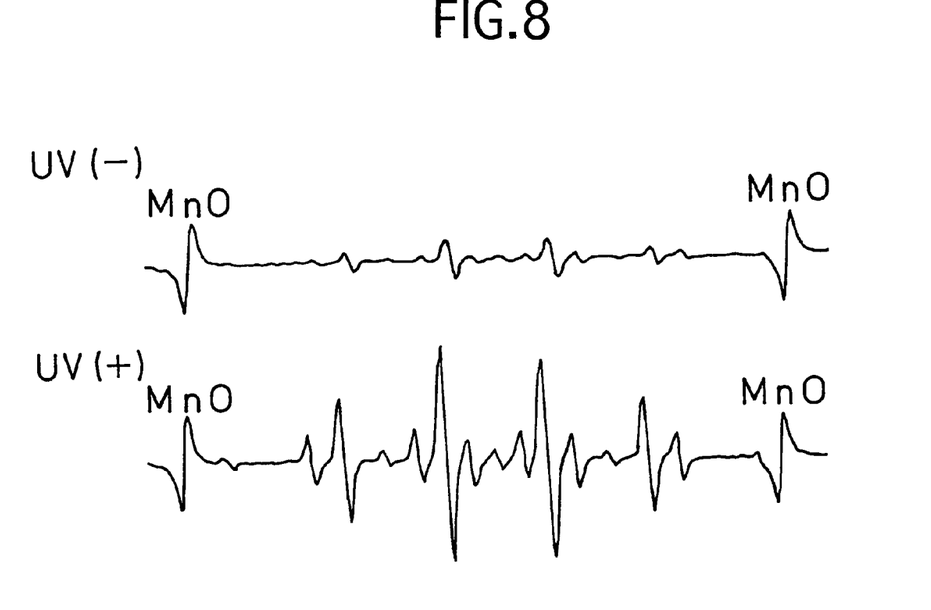
FIG. 8 is a chart showing the waveforms on perspiration C exuded in the far infrared radiation health appliance of the present invention.
Figure 9:
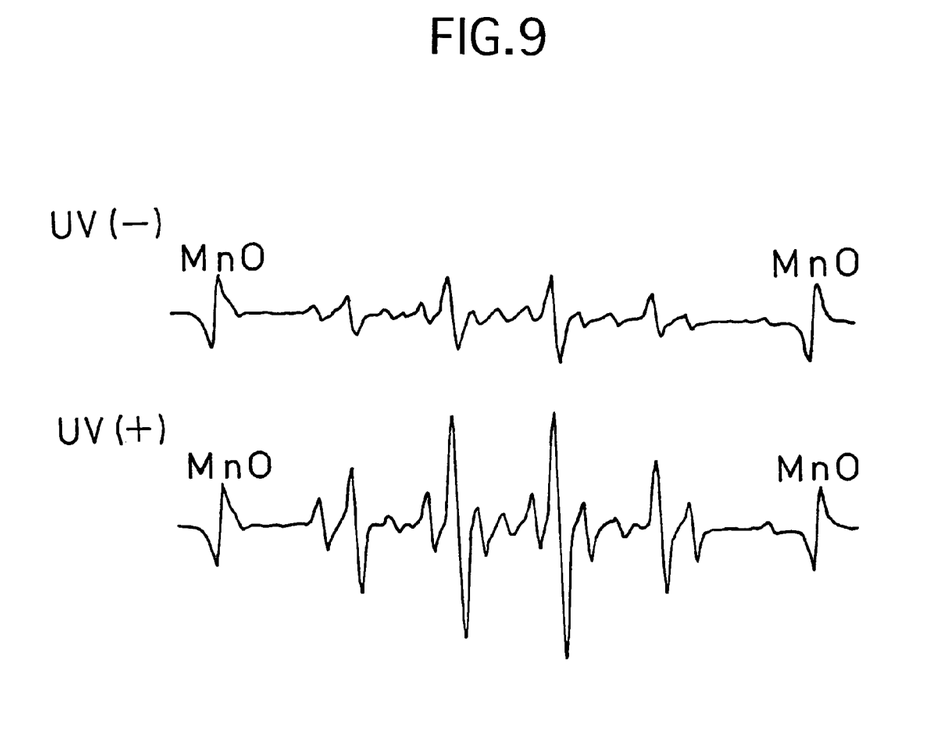
FIG. 9 is a chart showing the waveforms on perspiration D exuded in the far infrared radiation health appliance of the present invention.

FIGS. 6–9 show the ESR spectra of the respective samples. FIG. 6 shows the waveforms of the DMPO-trapped free radicals in the perspiration A exuded in a dry sauna, FIG. 7 the perspiration B exuded in a bath, and FIGS. 8 and 9 the perspirations C and D exuded in the far infrared radiation health appliance of the present invention. The UV(-) s show the waveforms before the ultraviolet irradiation, and the UV(+)s the waveforms after the ultraviolet irradiation.

The following Table 2 shows the signals of MnO in RIM, the signals of the samples in RIS, and RIS/RIM×100 in S/M (%), with MnO as the Control.

TABLE 2

| TYPE OF PERSPIRATION | UV | RIS | RIM | S/M (%) |
| --- | --- | --- | --- | --- |
| A | (-) | 15.8 | 156.0 | 10 |
|   | (+) | 55.6 | 159.2 | 35 |
| B | (-) | 30.8 | 161.2 | 19 |
|   | (+) | 142.6 | 160.2 | 89 |
| C | (-) | 72.0 | 163.2 | 44 |
|   | (+) | 373.2 | 161.0 | 232 |
| D | (-) | 170.0 | 153.2 | 111 |
|   | (+) | 473.4 | 161.6 | 293 |

The active oxygen in the perspiration A exuded in a dry sauna was as small as 10% without ultraviolet irradiation. It was 35%, or 3.5-times up, after the ultraviolet irradiation. The waveforms cannot be concluded of pure hydroxy radicals, but seem to be *OOH waveforms. The bath-exuded perspiration B was 19% before the ultraviolet irradiation, but was 89%, or 4.7-times up, after the ultraviolet irradiation. Hydroxy radical waveforms were obtained from the perspirations C and D exuded in the far infrared radiation health appliance of the present invention. The irradiated perspirations C and D were increased up to 5.2 times and 2.6 times, respectively, than before the ultraviolet irradiation. The S/M values were as great as 232% in C and 293% in D. As seen from above, the perspirations C and D exuded in the far infrared radiation health appliance of the present invention caused the greatest amounts of active oxygen. These analyses show that the far infrared radiation health appliance of the present invention is effective at egesting components that produce active oxygen in the body.

Now, it is well known that when a man takes a lying position, the head, heart, and toes become parallel against the gravity, with a three-times improvement of blood circulation than in a sitting position despite less burden on the heart. From old days, those who got sick heal lying abed, not sitting up. The far infrared radiation health appliance according to the present invention can apply far infrared rays to the whole body (up to the soles) of a user who is in a lying position which improves the blood circulation and metabolism. The head can be put in or out of the dome interior.

Outside the far infrared radiation health appliance of the present invention is air, which facilitate the expansion of peripheral blood capillaries in a warmed body. Thus, the blood circulation can be improved with a less burden on the heart and vessels. In this regard, the appliance differs completely from baths and spas in which the hot water presses a body from outside to hinder the capillary expansion. Accordingly, even those who have an injury in the blood circulation system or cerebral nerves can use the appliance with relative ease and safety.

Moreover, while a sauna could not be taken for more than 20 minutes, the far infrared radiation health appliance of the present invention can be used over 30 minutes with ease. Even 60 minutes of use will cause no trouble. Lowering the power allows a usage as a weightless blanket in which one can sleep, as well as an allergen-free blanket.

According to the far infrared radiation health appliance of the present invention, the cutaneous function can be activated to improve the cutaneous respiration and blood circulation for more active metabolism, thereby promoting two types of perspiration, namely, high volume of perspiration from perspiratory glands and sebum perspiration from sebaceous glands. In particular, toxic substances stored in the body, such as dioxins, can be egested from sebaceous glands effectively to contribute to health enhancement.

While there has been described what are at present considered to be preferred embodiments of the present invention, it will be understood that various modifications may be made thereto, and it is intended that the appended claims cover all such modifications as fall within the true spirit and scope of the invention.

What is claimed is:

1. A far infrared radiation health appliance comprising a plurality of semicylindrical members telescopically connected to each other for relative sliding movement in an axial direction, and carbon-black-containing planar heating elements serving as resistors arranged continuously over generally the entire inner surfaces of said semicylindrical members.

2. The far infrared radiation health appliance according to claim 1, wherein said planar heating elements are energizable and heatable to a temperature of 55–70° C.

3. A far infrared radiation health method comprising the steps of placing a user into a far infrared radiation health appliance according to claim 1 and subjecting the user to far infrared irradiation from said appliance to promote perspiration from perspiratory glands and egestion of sebum from sebaceous glands.

4. The far infrared radiation health method according to claim 3, wherein the planar heating element of the appliance is energized and heated to a temperature of 55–70° C.

5. The method of claim 4, further comprising the step of egesting dioxins together with perspiration and sebum from perspiratory glands.

6. The method of claim 4, further comprising the step of egesting active oxygen sources together with perspiration and sebum from perspiratory glands.

7. The method of claim 3, further comprising the step of egesting dioxins together with perspiration and sebum from perspiratory glands.

8. The method of claim 3, further comprising the step of egesting active oxygen sources together with perspiration and sebum from perspiratory glands.

9. A far infrared radiation health method comprising the steps of placing a user into a far infrared radiation appliance according to claim 1, and adjusting a power supply of said appliance to the planar heating element for radiating far infrared rays, so that the interior of the appliance is adjusted to a temperature not causing perspiration for a user or a temperature right below the point of perspiration for a user.

10. The appliance of claim 1, further comprising a generally planar support surface for supporting a user, the support surface comprising a far infrared ray reflective means.

11. The appliance of claim 10, wherein a first closed end arranged perpendicular to the axial direction of the semicylindrical members comprises a far infrared ray reflective means on a surface facing an interior of the appliance.

12. The appliance of claim 11, further comprising a second end arranged perpendicular to the axial direction of the semicylindrical members, opposite a first closed end, the second end being made of a flexible material and comprising an opening adjacent the support surface conforming generally to the outer peripheral shape of a neck of a user.

13. The appliance of claim 12, wherein the second end comprises a far infrared ray reflective means located continuously on a surface facing an interior of the appliance.

14. The appliance of claim 12, further comprising a sealing means arranged on an inside perimeter surface of a first semicylindrical dome arranged telescopically above a second semicylindrical dome, the sealing means sealingly contacting an outer perimeter surface of the second dome, and formed to allow telescopic sliding motion between the first dome and second dome.

15. The appliance of claim 11, wherein the inner surfaces of said semicylindrical members are in the form of concave mirrors which focus on a longitudinal center line of a user.

16. The appliance of claim 1, wherein the inner surfaces of said semicylindrical members are in the form of concave mirrors which focus on a longitudinal center line of a user.

17. The appliance of claim 1, further comprising a sealing means arranged on an inside perimeter surface of a first semicylindrical dome arranged telescopically above a second semicylindrical dome, the sealing means sealingly contacting an outer perimeter surface of the second dome, and formed to allow telescopic sliding motion between the first dome and second dome.

* * * * *